United States Patent
Riley (12)

(10) Patent No.: US 6,283,972 B1
(45) Date of Patent: Sep. 4, 2001

(54) HOLDER FOR ACETABULAR REAMER

(75) Inventor: Edward J. Riley, Falmouth, ME (US)

(73) Assignee: Riley Medical, Inc., Auburn, ME (US)

( * ) Notice: Subject to any disclaimer, the term of this patent is extended or adjusted under 35 U.S.C. 154(b) by 0 days.

(21) Appl. No.: 09/696,606

(22) Filed: Oct. 25, 2000

(51) Int. Cl.$^7$ ................................................. A61B 17/00
(52) U.S. Cl. ................................. 606/81; 606/86; 606/80
(58) Field of Search ................................. 606/79, 80, 81, 606/82, 83, 84, 85, 86, 87, 88, 180; 623/22.21, 22.31, 22.32, 22.39; 408/14; 407/54, 61

(56) References Cited

U.S. PATENT DOCUMENTS

| | | | | |
|---|---|---|---|---|
| 4,611,587 | * | 9/1986 | Powlan | 606/81 |
| 5,501,686 | * | 3/1996 | Sayler | 606/83 |
| 5,658,290 | * | 8/1997 | Lechot | 606/80 |
| 5,817,096 | * | 10/1998 | Sayler | 606/81 |
| 5,976,148 | * | 11/1999 | Charpenet et al. | 606/81 |
| 5,980,170 | * | 11/1999 | Sayler | 606/80 |

* cited by examiner

Primary Examiner—Pedro Philogene

(57) ABSTRACT

A holder for an acetabular reamer of the type including a generally hemispherical shell having a circular edge and cross arms connected adjacent to the edge and which converge at the center of the edge. The holder includes a base having a datums and at least three pedestals extending up from the base at locations spaced radially from, and distributed about, the datums. Each pedestal has side walls and an upper wall extending between the side walls and facing away from the base. The upper wall is curved so that together the upper walls of the pedestals define an imaginary surface having substantially spherical curvature, so that the pedestals help to retain a reamer whose shell is congruent to the collective upper walls and whose edge is substantially parallel to the base.

14 Claims, 2 Drawing Sheets

HOLDER FOR ACETABULAR REAMER

This invention relates to a medical holding device. It relates more particularly to a holder for an acetabular reamer.

BACKGROUND OF THE INVENTION

FIELD OF THE INVENTION

An acetabular reamer is a bone-cutting tool which is rotated by a motorized driver. As shown in FIG. 1, a reamer R is basically a hemispherical metal shell S usually of stainless steel whose surface is formed with a multiplicity of holes H defining outwardly protruding cutting edges E. A pair of rigid cylindrical rods forming cross arms A are connected adjacent to the edge margin of the shell S. These cross arms are used to releasably connect the reamer R to the rotary shaft of a driving tool (not shown).

When not in use, acetabular reamers normally repose in a tray which protects them to some extent during sterilization and handling. However, they are still free to move about within the tray which could result in damage to the cutting edges of the reamers. Also, since they are free to move within the tray, they may have various orientations making it more difficult to grasp and attach successive reamers to the driving tool.

SUMMARY OF THE INVENTION

Accordingly, it is an object of the invention to provide a holder for an acetabular reamer which fixes the orientation of the reamer.

Another object of the invention is to provide such a holder which releasably secures the reamer to the bottom wall of a tray or other support surface.

A further object of the invention is to provide a holder of this type which presents a selected side of the reamer to a surgeon or other user.

Yet, another object of the invention is to provide a holder for an acetabular reamer which is relatively easy and inexpensive to manufacture in quantity.

Other objects will, in part, be obvious and will, in part, appear hereinafter. The invention accordingly comprises the features of construction, combination of elements and arrangement of parts which will be exemplified in the following detailed description, and the scope of the invention will be indicated in the claims.

Briefly, my holder is adapted to support an acetabular reamer of the type which has a generally hemispherical shell with a single circular edge and rigid cross arms connected adjacent to that edge. The holder includes a base having a central datums and at least three pedestals extending up from the base at locations space radially from and distributed about the datums. Each pedestal has side walls and an upper wall facing away from the base, the upper wall being curved so that, together, the upper walls of the pedestals define an imaginary surface having spherical curvature. The pedestals are adapted to guide or support a reamer whose shell is congruent to the collective upper walls of the pedestals and whose edge is substantially parallel to the base.

In one preferred embodiment of the holder, the upper walls of the pedestals are concave and arranged to support a reamer, shell-side-down, so that the cross arms of the reamer face away from the base.

In a second preferred holder embodiment, the upper walls of the pedestals are convex and the pedestals are cylindrically curved about the datums. In addition, each upper wall has a radially outer bevel and a crown so that each pedestal is lower at the side walls thereof than at the crown. Also, a pair of clips extend up from the base at locations spaced radially from and distributed about the datums. These clips have open mouths and are arranged and adapted to receive and releasably retain a confronting pair of cross arms of a reamer. Preferably, the pedestals are angularly offset from the clips and the clips are no higher than the side walls of the pedestals. Resultantly, when a reamer is juxtaposed to the holder so that the reamer cross arms engage the upper walls of the pedestals, the cross arms slide along those edges and rotate the reamer until the cross arms are aligned with the mouths of the clips, whereupon the reamer can be pressed down until the cross arms are resiliently received in the clips.

Preferably, the base of each holder includes means for releasably fastening the base to a support surface such as the bottom wall of a sterilization tray. In its simplest form, the fastener means may be a through hole in the base at the datums and a fastener arranged and adapted to extend through that hole and into the support surface.

As it will become apparent, the holder may be a unitary molded plastic part which can be manufactured in quantity at relatively low cost.

BRIEF DESCRIPTION OF THE DRAWINGS

For a fuller understanding of the nature and the objects of the invention, reference should be made to the following detailed description, taken in connection with the accompanying drawings, in which.

DESCRIPTION OF ILLUSTRATIVE EMBODIMENTS

Figure 2:
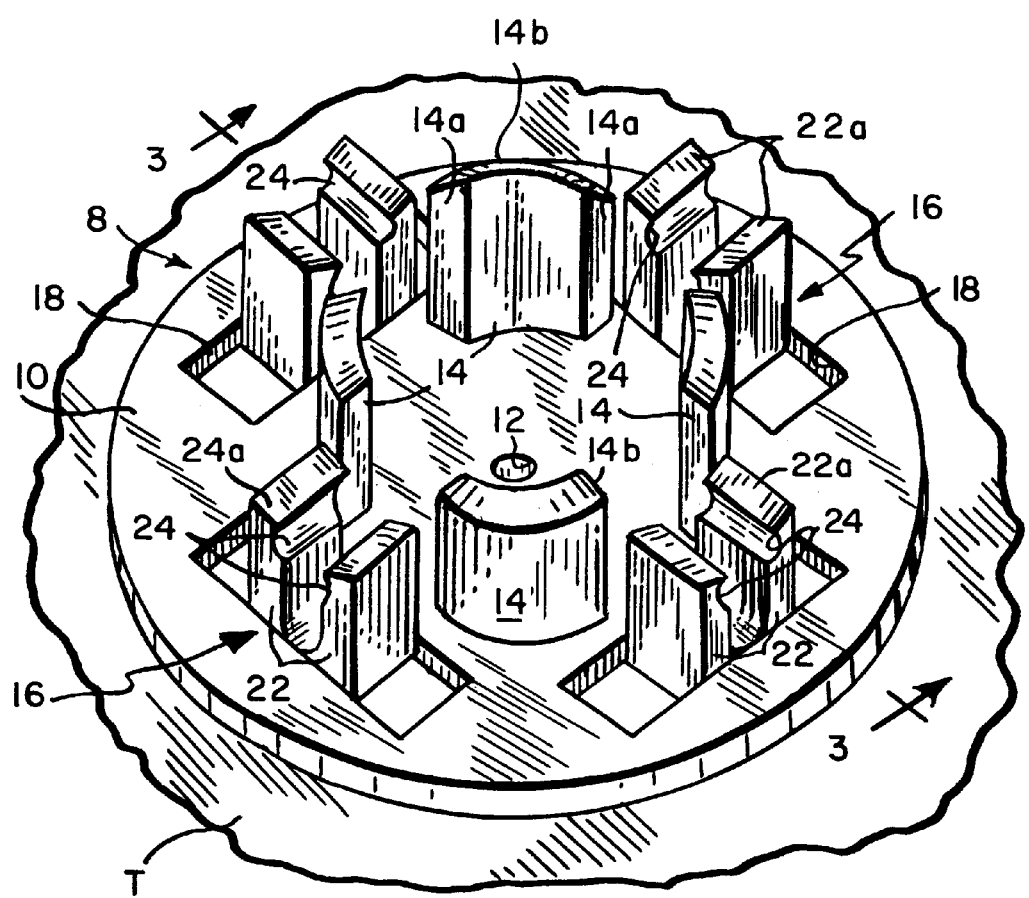
FIG. 2 is a perspective view on a larger scale of a holder for holding the reamer depicted in FIG. 1, the holder being fastened to a tray.
Figure 3:
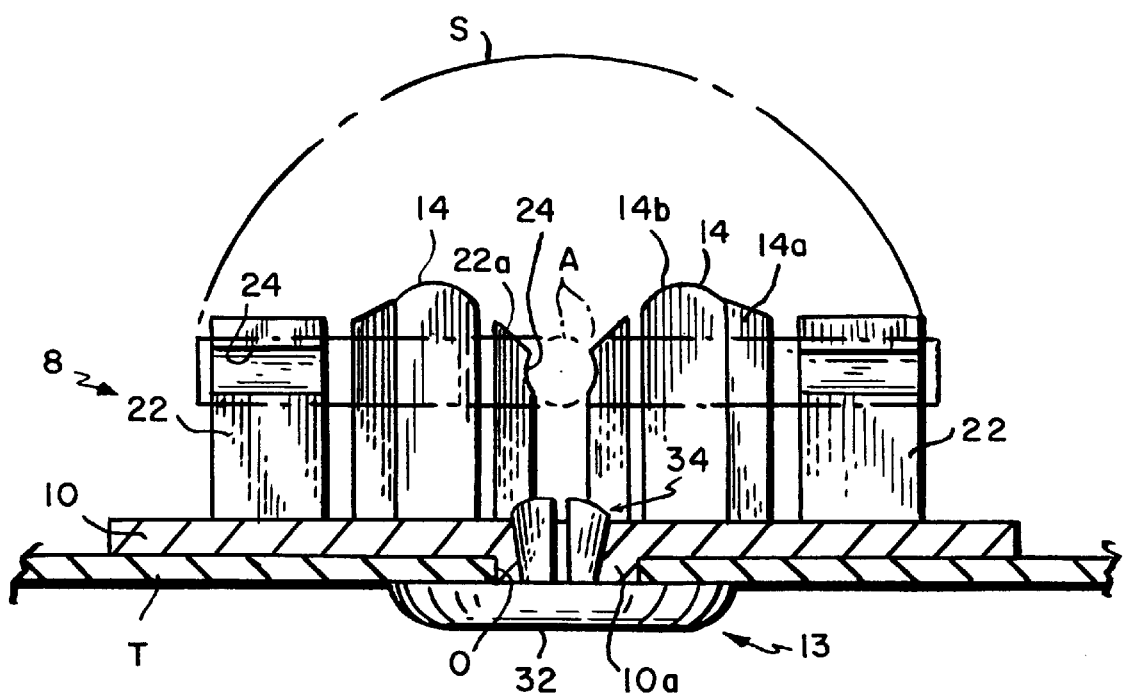
FIG. 3 is a sectional view on a larger scale taken along line 3—3 of FIG. 2.

Referring to FIGS. 2 and 3 of the drawings, a preferred embodiment of my holder, shown generally at 8, comprises a base 10. Although, the base may be practically any shape, the illustrated one is a circular disk having a center defining a datums. Preferably, a through hole 12 is provided at the center of base 10, i.e., at the datums, and a collar 10a may be provided around that hole at the underside of the base. In use, collar 10a may key into an opening O in the bottom wall of a tray T or other support surface as shown in FIG. 3. Base 10 may be releasably anchored to tray T by a fastener 13 as shown in that same figure.

Formed integrally to base 10 is a plurality of upstanding pedestals 14 distributed about hole 12. The illustrated holder has two pairs of diametrically opposite pedestals 14 centered on hole 12, the two pairs of pedestal being angularly offset by 90°. It should be understood that the holder may have more or fewer such pedestals 14; however, it is preferred that there be at least three such pedestals distributed about the central datums.

As shown in FIGS. 2 and 3, each pedestal 14 has side walls 14a and an upper wall 14b extending between those side walls. The illustrated pedestals have cylindrical curvature about the central datums, i.e. hole 12, so that the upper wall 14b of each pedestal constitutes a sector of an annulus. Furthermore, each pedestal is beveled and rounded so that the upper wall 14b faces radially outward and is crowned so that the pedestal is shorter at the side walls thereof than at the crown. Actually, taken together, the upper walls 14b of the pedestals 14 define an imaginary surface having substantially spherical curvature which corresponds more or less to the curvature of the reamer shell S depicted in FIG. 1. As we shall see, those pedestals may function as guides to facilitate properly seating a reamer in the holder 8.

Still referring to FIGS. 2 and 3, also formed integrally with base 10 is a plurality of clips shown generally at 16. Clips 16 extend up from base 10 at locations spaced radially from the central datums and are angularly offset from pedestals 14. While the illustrated holder 8 has two pairs of diametrically opposite clips 16 angularly offset by 90°, the holder embodiment may have as few as two such clips. Preferably, clips 16 are located radially outboard on base 10 from pedestals 14 so that they can be molded along with the base using die parts (not shown) which extend through base 10 leaving the openings 18 therein.

Each clip 16 comprises a pair of spaced apart, relatively resilient, mirror image legs 22. Preferably, legs 22 extend up from the base a distance which is no higher than the side walls 14a of pedestals 14. Preferably also, the top walls 22a of the legs 22 comprising each clip 16 are oppositely beveled as shown to define the mouth of the clip. Also, a pair of radially extending grooves 24 are formed in the opposing walls of each pair of legs 22. Each clip 16 is arranged and adapted to resiliently receive and engage one of the cross arms A of the reamer R depicted in FIG. 1.

Figure 1:
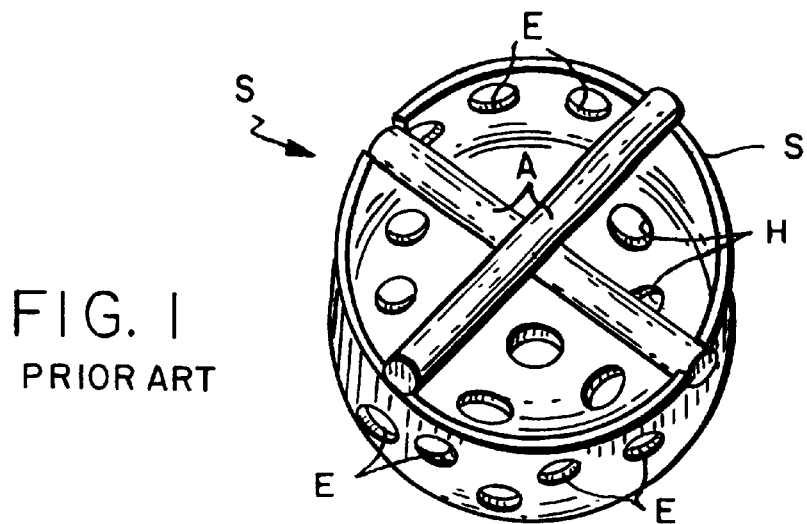
FIG. 1, already described, is a perspective view of a conventional acetabular reamer.

As shown in FIG. 2, the grooves 24 of each diametrically opposite of pair of clips 16 are collinear so that if the reamer R illustrated in FIG. 1 is juxtaposed to the holder 8 with the cross arms A of the reamer being aligned with the mouths of the clips, the reamer may be pressed toward base 10 until the cross arms A resiliently engage in grooves 24. Obviously, the spacing of the upper walls 22a of the clip legs 22 of each clip 16 is somewhat less than the diameter of cross arms A so that the legs have to be forced apart to some extent before the cross arms can engage in the grooves 24. The fact that the upper walls 22a are beveled facilitates the seating of the cross arms in the clips 16.

It is a feature of the holder 8 depicted in FIGS. 2 and 3 that the holder is self aligning in that if a reamer R is positioned on the holder without the reamer cross arms A being aligned with the clips 16, the reamer will be rotated automatically about its axis under the influence of gravity until the cross arms of the reamer are in alignment with the mouths of the clips. That is, if the cross arms A of the reamer R are not aligned with the clips, they will rest on or engage the upper walls of 14b of pedestals 14. Since those upper walls are beveled and crowned as described above, they function as guide surfaces for the cross arms A. In other words, the weight of the reamer will cause the arms to rotate about their point of intersection as they slide down the convex walls 14b towards the side walls of the pedestals and thence to the clip mouths defined by the beveled upper edges 22a. At that point, the reamer can be pressed toward the base of the holder until the cross arms A of the reamer are engaged by the clips 16.

When it comes time to use the reamer R, it may be disconnected from the holder simply by pulling it away from base 10 with sufficient force to spread apart the legs 22 of clips 16 enough to release the cross arms A of the reamer.

A plurality of different size holders 8 may be fastened to a sterilization tray T as shown in FIGS. 2 and 3 to support the number of reamers R that may be necessary for a given surgical procedure, the main goal being to prevent the cutting edges E of the reamers from being damaged during the sterilization process or during handling. However, there is an ancillary benefit in that holders maintain the reamers in a consistent orientation within the tray so that they are always presented in the same way to the operating room person who has to attach successive reamers to a driving tool.

Figure 4:
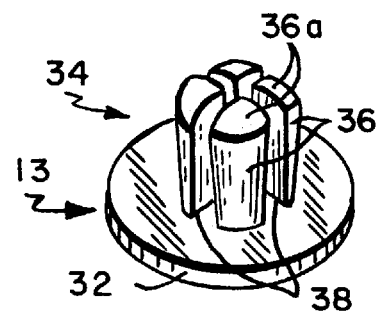
FIG. 4 is a perspective view on a much smaller scale of the holder fastener depicted in FIG. 3.

Refer now to FIG. 4 which shows the fastener 13 in greater detail. As seen there, it comprises a discoid head 32 and an elongated shaft 34 extending from the head, the shaft being split into four sectors 36a separated by cross-slits 38. The free ends 36a of the shaft sectors are rounded and the shaft 34 as a whole is tapered, so that the root of the shaft has a smaller diameter than the free end thereof. Likewise, as shown in FIG. 3, the hole 12 in the holder base 10 has a taper which is substantially the same as that of the fastener shaft 34. Thus, when the holder base 10 is positioned against the tray T with the hole 12 aligned with the opening O in the tray, the holder may be secured to the tray by pushing the fastener 13, shaft-end-first, through the opening O in the tray and into the tapered hole 12 in base 10. The sectors 36 of the fastener shaft 34 will be pressed together sufficiently to enable the shaft to extend into the smaller diameter lower end of hole 12 in base 10. When the fastener is seated, those sectors will resume their unstressed spread-apart condition within the hole 12 thereby anchoring base 10 to tray T.

Figure 5:
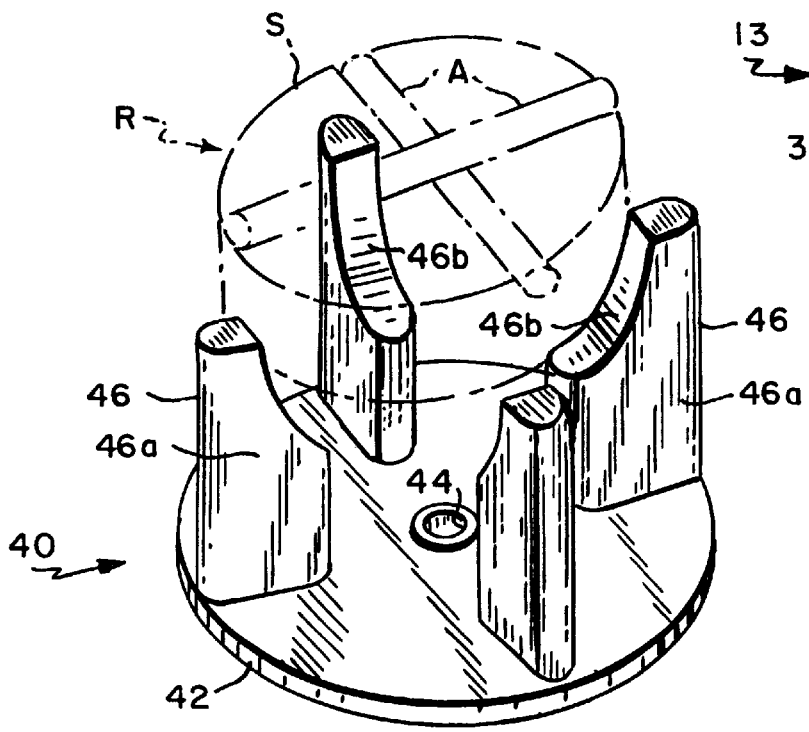
FIG. 5 is view similar to FIG. 2 of another holder embodiment.

Refer now to FIG. 5, which shows generally at 40 another holder embodiment for retaining a reamer R such that the cross arms A of the reamer face away from the holder. As seen there, holder 40 comprises a base 42 having a central datums which may be marked by a through hole 44. Spaced radially out from and distributed around that datums is a plurality, herein four, upstanding pedestals 46. Each pedestal has opposite side walls 46a and a concave upper wall 46b facing away from base 42 that extends between side walls 46a. Together, the upper walls 46b of all of the pedestals 46 define an imaginary surface having substantially spherical curvature which preferably conforms to the curvature of the reamer shell S depicted in FIG. 1. Resultantly, the holder 40 can stably retain a reamer R, shell-side-down, with its circular edge parallel to base 42, as shown in phantom in FIG. 5. In this way, the cross arms A of the reamer are presented for ready attachment to the working end of a rotary driver.

Since the curvature of the pedestal upper walls 46b of holder 40 should be fairly closely related to the curvature of the reamer shell S supported by the holder, the holder may be made in several sizes. Alternatively, to minimize cost, holder 40 may be made in one or two standard sizes with generally rectangular pedestals 46 which may then be cut to form concave upper walls 46b that will conform to the curvature of the reamer actually to be supported by a particular holder.

Like holder 8, holder 40 may be releasably attached to a tray or other support surface by a fastener 13 or other suitable fastening means such as a screw, peg or the like.

It will be apparent from the foregoing that the holders 8 and 40, as well as the fastener 13, may be formed by injection molding using a suitable autoclavable, rigid or semi-rigid elastomer. The latter material is preferred because it is softer and less apt to damage the cutting edges E of a reamer R reposing in the holder. Thus, my holder can be made in quantity at relatively low cost.

It will thus be seen that the objects set forth above, among those made apparent from the preceding description, are efficiently attained. Also, certain changes may be made in the above constructions without departing from the scope of the invention. Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A holder for an acetabular reamer of the type including a generally hemispherical shell having a circular edge and cross arms connected adjacent to said edge and which converge at the center of said edge, said holder comprising a base having a datums, and at least three pedestals extending up from said base at locations spaced radially from, and distributed about, said datums, each said pedestal having side walls and an upper wall extending between said side walls and facing away from the base, said upper wall being curved so that, together, the upper walls of the pedestals define an imaginary surface having substantially spherical curvature, said pedestals helping to retain a reamer whose shell is more or less congruent to said collective upper walls and whose edge is substantially parallel to said base.

2. The holder defined in claim 1 wherein said upper walls are convex.

3. The holder defined in claim 2 wherein each pedestal is cylindrically curved about said datums and each upper wall has a radially outer bevel and is crowned so that the pedestal is lower at said side walls than at the crown.

4. The holder defined in claim 2 or 3 and further including at least one pair of clips extending up from the base at locations spaced radially from, and distributed about, said datums, said clips having mouths facing away from the base and being arranged and adapted to receive and releasably retain the cross arms of a reamer whose shell is congruent to the collective upper walls of said pedestals.

5. The holder defined in claim 4 wherein said at least three pedestals include a first pair of diametrically opposite pedestals, and a second pair of diametrically opposite pedestals, said first and second pedestal pairs being angularly offset 90° about said datums.

6. The holder defined in claim 5 wherein the pedestals are angularly offset from, but adjacent to, the clips, and the clips are no higher than the side walls of the pedestals so that when a reamer is placed on the holder so that the reamer cross arms engage the upper walls of the pedestals, the weight of the reamer will cause the cross arms to slide down said upper walls until the cross arms are aligned with the mouths of said clips.

7. The holder defined in any one of claims 1 to 3 and further including fastening means for fastening the holder to the support.

8. The holder defined in claim 7 wherein the fastening means comprise a rough hole in said base at said datums, and a fastener sized to extend into the hole to fasten the base to a support.

9. The holder defined in claim 8 wherein said hole is tapered and said fastener comprises a head and a split shaft extending from the head, said shaft being tapered correspondingly to said hole.

10. The holder defined in claim 1 wherein said upper walls are concave.

11. The holder defined in claim 10 wherein said at least three pedestals include a first pair of diametrically opposite pedestals and a second pair of diametrically opposite pedestals, said first and second pedestal pairs being angularly offset 90° about said datums.

12. The holder defined in claim 7 and further including fastening means for fastening said holder to a support.

13. The holder defined in claim 12 wherein said fastening means includes a through hole in said base at said datums, and a fastener sized to extend into said hole to fasten the base to a support.

14. The holder defined in claim 13 wherein said hole is tapered, and said fastener comprises a head and a split shaft extending from the head, said shaft being tapered are correspondingly to said hole.

* * * * *